United States Patent
Puopolo et al.

(10) Patent No.: US 8,152,531 B1
(45) Date of Patent: Apr. 10, 2012

(54) TEAM-BASED FITNESS CHALLENGE SYSTEM AND METHOD

(75) Inventors: Paul Puopolo, Louisville, KY (US); Sandra Jean Nelson, Louisville, KY (US)

(73) Assignee: Humana Inc., Louisville, KY (US)

( * ) Notice: Subject to any disclaimer, the term of this patent is extended or adjusted under 35 U.S.C. 154(b) by 908 days.

(21) Appl. No.: 12/192,447

(22) Filed: Aug. 15, 2008

(51) Int. Cl.
*A63F 9/24* (2006.01)

(52) U.S. Cl. .............................. 434/247; 463/7

(58) Field of Classification Search .......... 434/247–255; 463/7, 42
See application file for complete search history.

(56) References Cited

U.S. PATENT DOCUMENTS

| | | | |
|---|---|---|---|
| 5,879,163 A | 3/1999 | Brown et al. | |
| 5,960,403 A * | 9/1999 | Brown | 705/2 |
| 6,167,362 A | 12/2000 | Brown et al. | |
| 6,210,272 B1 | 4/2001 | Brown | |
| 6,379,253 B1 | 4/2002 | Nishioka | |
| 7,092,846 B2 | 8/2006 | Vock et al. | |
| 2006/0089840 A1* | 4/2006 | May | 705/1 |
| 2008/0015089 A1* | 1/2008 | Hurwitz et al. | 482/8 |

OTHER PUBLICATIONS

Puopolo, Paul, Humana Games for Health: From the real world to the digital, PowerPoint Presentation, Jun. 11, 2008, 24 pages.
Join Humana in our pursuit to motivate and create active students, HorsePower Challenge, Mar. 31, 2008, one page.

* cited by examiner

*Primary Examiner* — Omkar Deodhar
(74) *Attorney, Agent, or Firm* — Standley Law Group LLP (57) ABSTRACT

A fitness challenge program designed to encourage physical activity as well as to entertain and engage participants. Individuals are organized into teams and compete individually as well as against other teams. The program incorporates the use of computer technology to record physical activity and track progress for individuals as well as their teams. The individual and team activity information is posted to a web site accessible to the participants. Each participant has an account and can access his or her activity data through the web site. Team progress can also be viewed in the form of activity level data as well as movement to various locations associated with activity levels. The program incorporates educational content that is tied to team progress in the challenge. The program may be organized and administered through the middle schools that student participants attend.

20 Claims, 7 Drawing Sheets

TEAM-BASED FITNESS CHALLENGE SYSTEM AND METHOD

CROSS-REFERENCE TO RELATED APPLICATIONS

None.

FIELD OF THE INVENTION

The present invention relates generally to fitness programs. In particular, the present invention relates to a team-based fitness challenge system and method in which data for a fitness activity performed by individuals on different teams is collected by an electronic device and uploaded to a database where it is compiled and analyzed. A winner of the fitness challenge may be determined by combining activity levels for participants on each team.

BACKGROUND OF THE INVENTION

In many countries, playing of computer and video games and other sedentary activities such as watching movies and television have become the preferred pastimes of school-aged children. The problem is especially prevalent in middle school aged children who are entering their teen years or are in their early teen years. Playgrounds and play equipment designed for younger children that provide entertainment as well as an opportunity for physical activity are no longer of interest to middle school-aged children. There are few equivalents or substitutes for older children that allow for a similar level of physical activity while also providing some entertainment. As a result, the children increasingly engage in other less physically demanding or even passive activities during their free time.

Another reason that middle school-aged children may be less active than they were during their elementary school years is that they have less free time. Homework and extra-curricular demands in school increase with each grade so that the children typically devote more time to studying and other school activities and less time to playing or other physical activities. Competing demands for a student's time can make it difficult for the student to find time to exercise or engage in a physically demanding activity. Furthermore, it is unlikely that they will try to find or make time to exercise. Even if they understand that exercise is important, they are unlikely to perform physical activities for the sole purpose of maintaining or improving their health. They still have a need to be entertained or engaged when performing any activity, whether physical or mental. Therefore, there is a need for a physical activity program for middle school aged children that encourages exercise and provides entertainment.

SUMMARY OF THE INVENTION

The present invention is a fitness challenge program for middle school students that is designed to encourage physical activity as well as to entertain and engage participants. Students are organized into teams and compete individually as well as against other teams toward a goal. The program incorporates the use of computer technology to record activity and track progress for individuals as well as their teams. The individual and team activity information is posted to a web site accessible to the students. The program also incorporates educational content that is tied to team progress in the challenge. The program may be organized and administered through the middle schools that the children attend.

In an example embodiment, the fitness activity that students perform is walking so that virtually all students in the school can participate. Students from a particular middle school are on the same team and they complete against student teams from other middle schools in the area. Each participating student is provided with a pedometer that records the number of steps he or she takes every day and that communicates the step data wirelessly to a remote access point located at the student's school. The step data for each student is uploaded to a server at the school and then to another server and website where it is stored in a database that records step data for all participating schools. Each student has an account and can access his or her step data through the web site.

In the example embodiment, each student has a screen character representation that is a horse. Students have the ability to customize their horses based on activity accomplishments. Each school or team is represented by a bus that passes checkpoints in relation to the school's student step activity. The combined activity level of the team's students determines movement of the bus around the world. Students can view information about world checkpoints that the buses pass as their movement around the world is tracked. The winner of the challenge is the school with the highest level of activity and therefore, the bus that travels the farthest.

DETAILED DESCRIPTION

Figure 1:
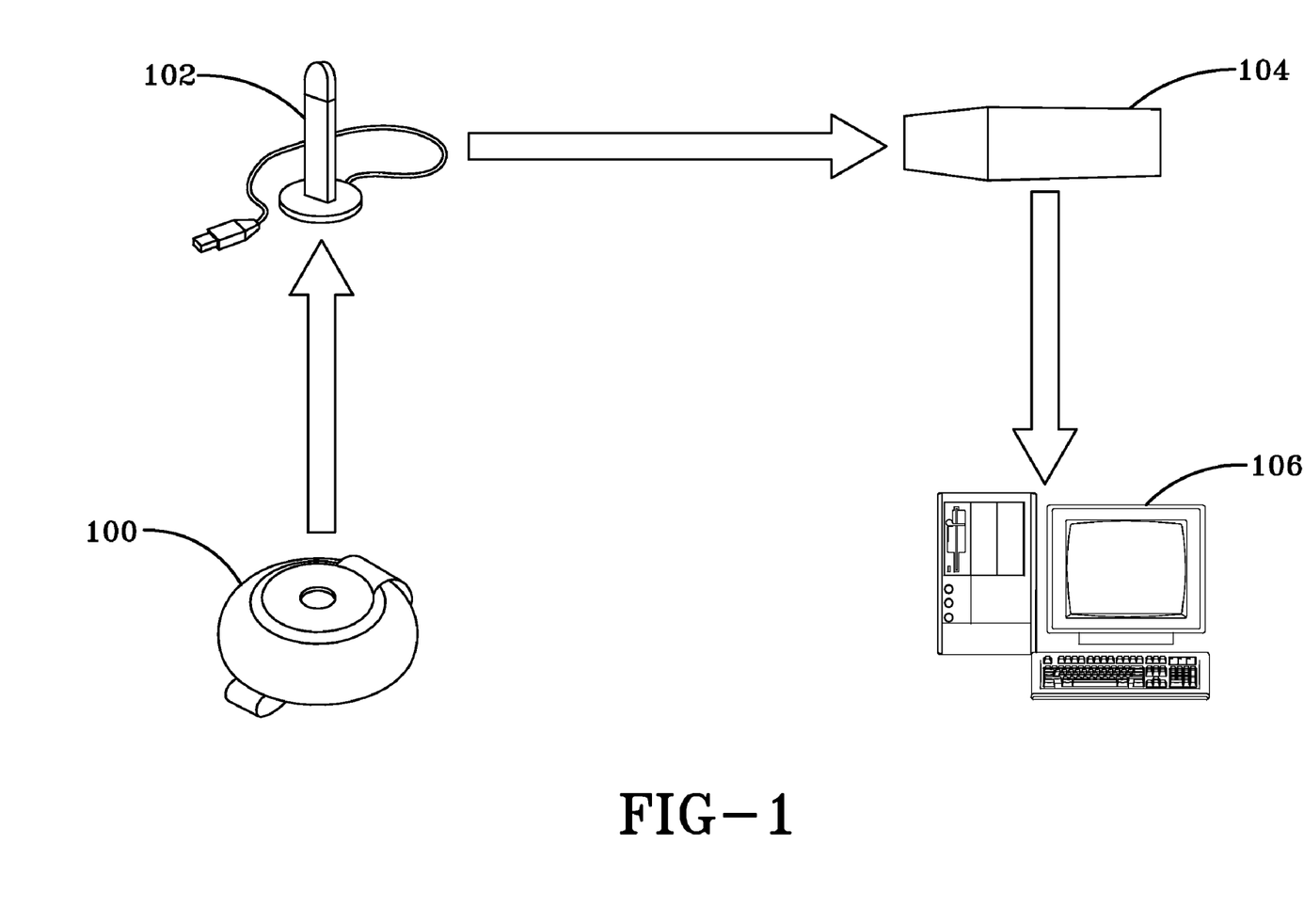
FIG. 1 is a diagram of the primary hardware components for a fitness challenge program.

Referring to FIG. 1, a diagram of the primary hardware components for a fitness challenge program according to an example embodiment is shown. A pedometer 100 captures step activity for a period of time. In an example embodiment, an Actiped™ fitness monitor from Fitlinxx® is used to capture step data for up to two weeks. The monitor connects wirelessly to a remote access point 102 when in range. A remote access point 102 is installed in each participating school. The remote access point 102 is connected to a server 104 via a USB port. When a pedometer 100 is in range, the remote access point 102 captures the pedometer identifier and step data and transfers it to a database at the server 104. Step data for each student collected at the server 104 is transported across a secure wireless network using a web services application to a custom web application on another server 106 that records and tracks the data for each school, updates the challenge status, and that supports student and team access to the data.

Figure 2:
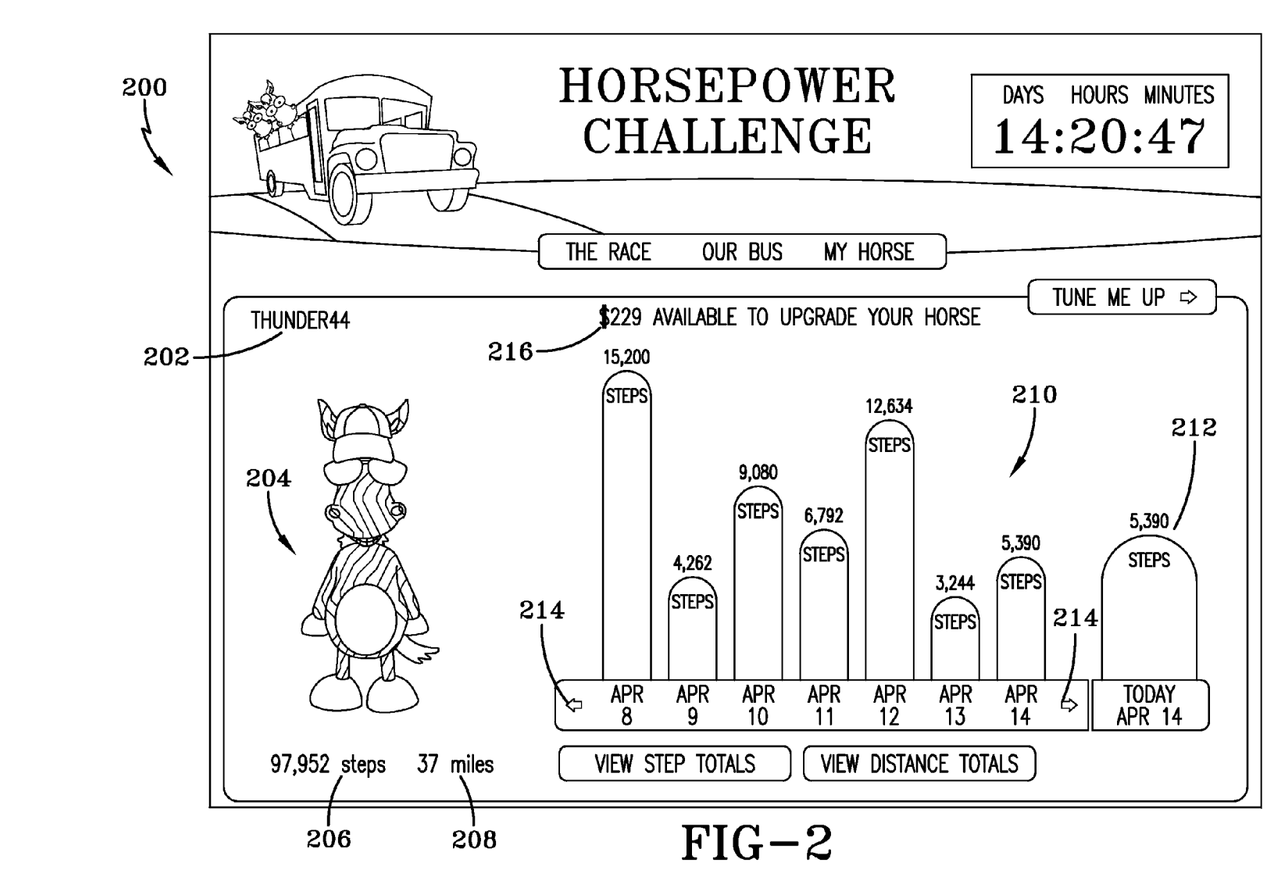
FIG. 2 is a sample student user screen for an example embodiment.

Referring to FIG. 2, a sample student user screen for an example embodiment is shown. The screen 200 displays the student's user name 202, customized challenge screen character or representative 204, step total 206 as recorded by the pedometer, number of miles as determined by the number of steps 208, daily step totals for a period of time 210, and total steps for the day 212. The student user can select left and right scroll buttons 214 to view earlier and later daily step totals. Finally, the screen displays the amount available to the student to upgrade the screen character 216. The student may earn points based on the recorded number of steps to purchase optional items for customizing his or her screen character. For example, the student may purchase accessories for the character, change colors, and change features. Each item may have an associated point cost that is deducted from the student's point total when a purchase is made.

Figure 3:
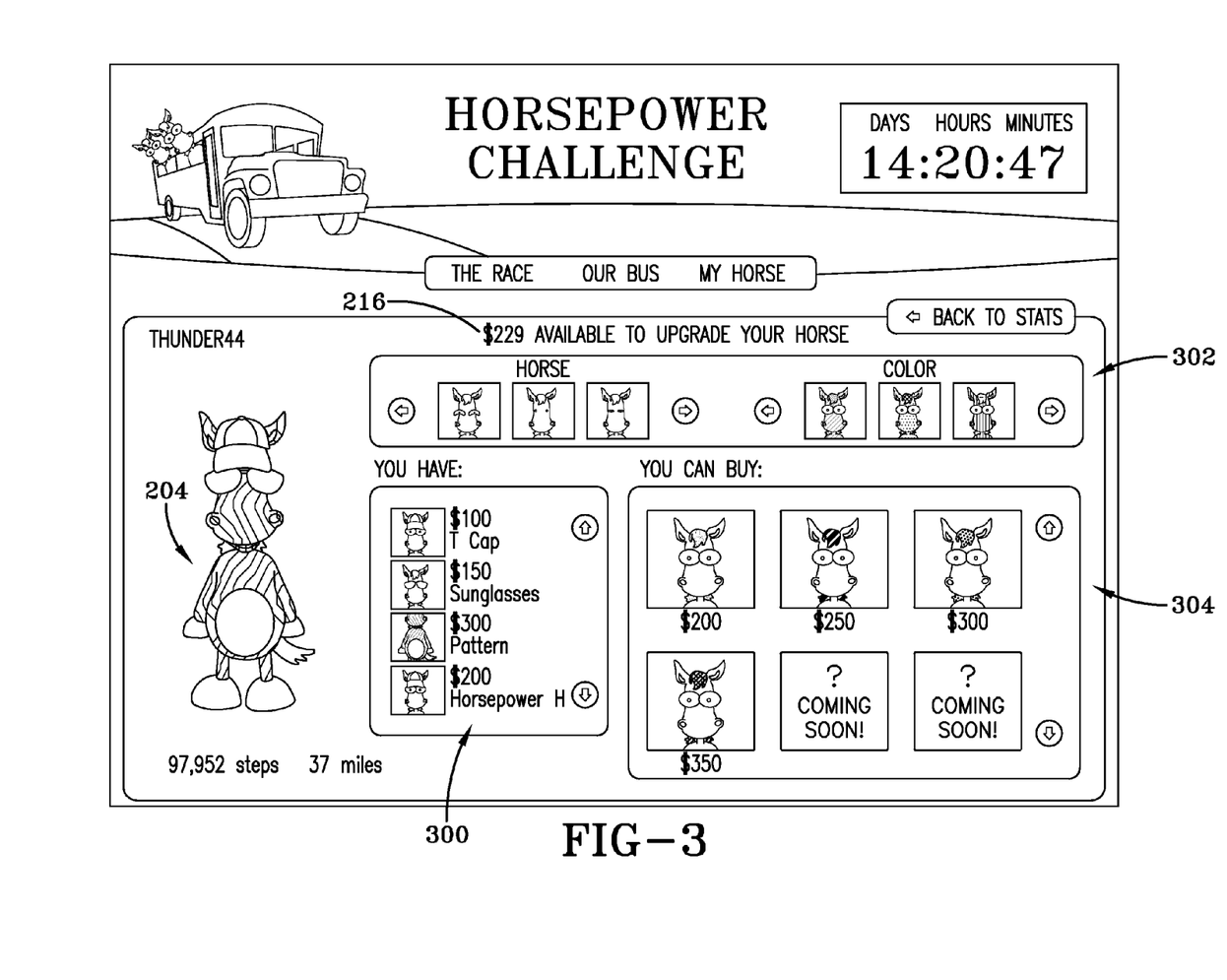
FIG. 3 is a sample character upgrade screen for an example embodiment.

Referring to FIG. 3, a sample character upgrade screen for an example embodiment is shown. The screen displays the student user's screen character 204 with its current upgrades and provides a scrolling list of the upgrades that the student has already purchased 300. The screen also indicates the amount available to the student for upgrades 216. Finally, the screen displays a scrolling list of upgrade options organized in groups or categories 302 as well as a detailed listing of upgrade options within a particular group or category 304. Upgrade options that the student selects are then applied to subsequent displays of the screen character.

Figure 4:
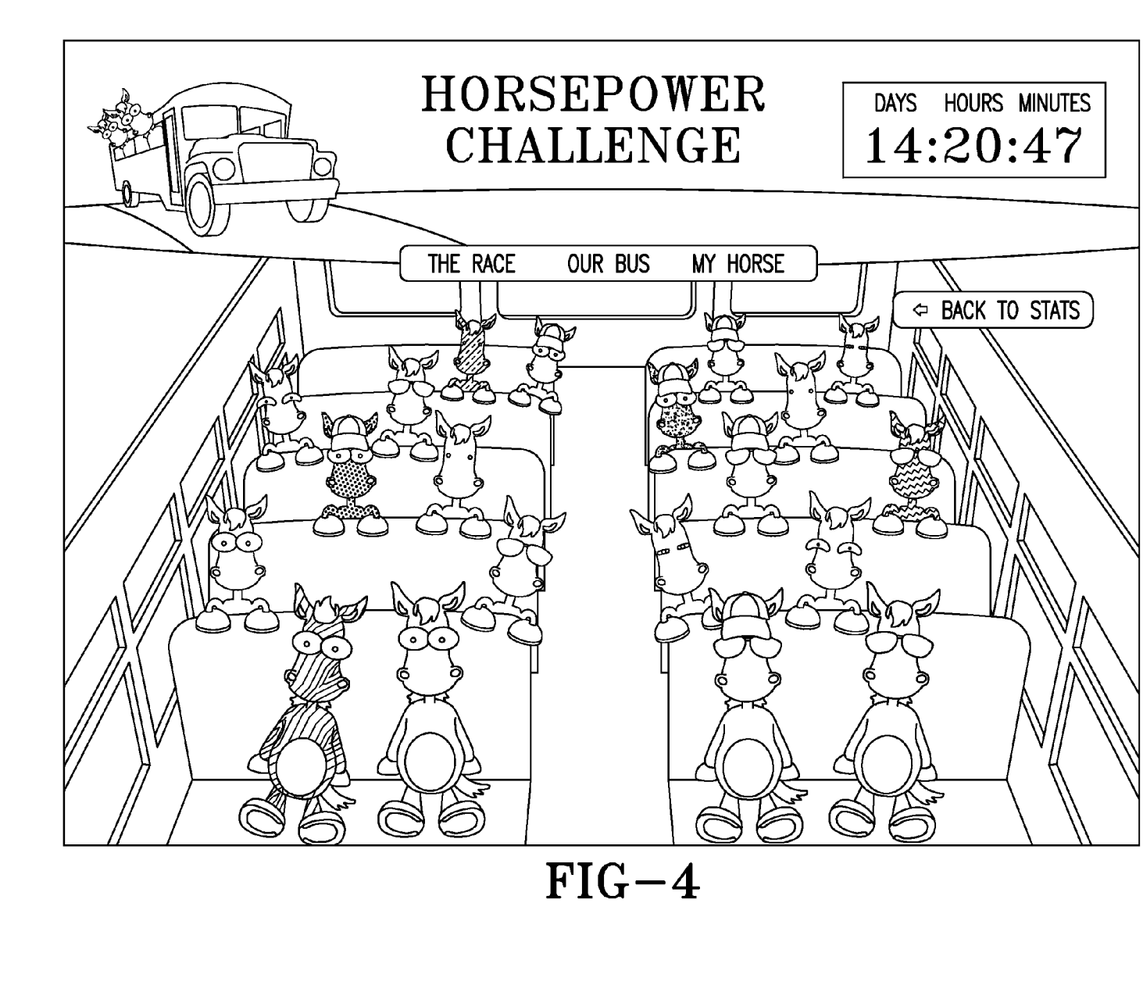
FIG. 4 is a sample bus screen for an example embodiment.
Figure 5:
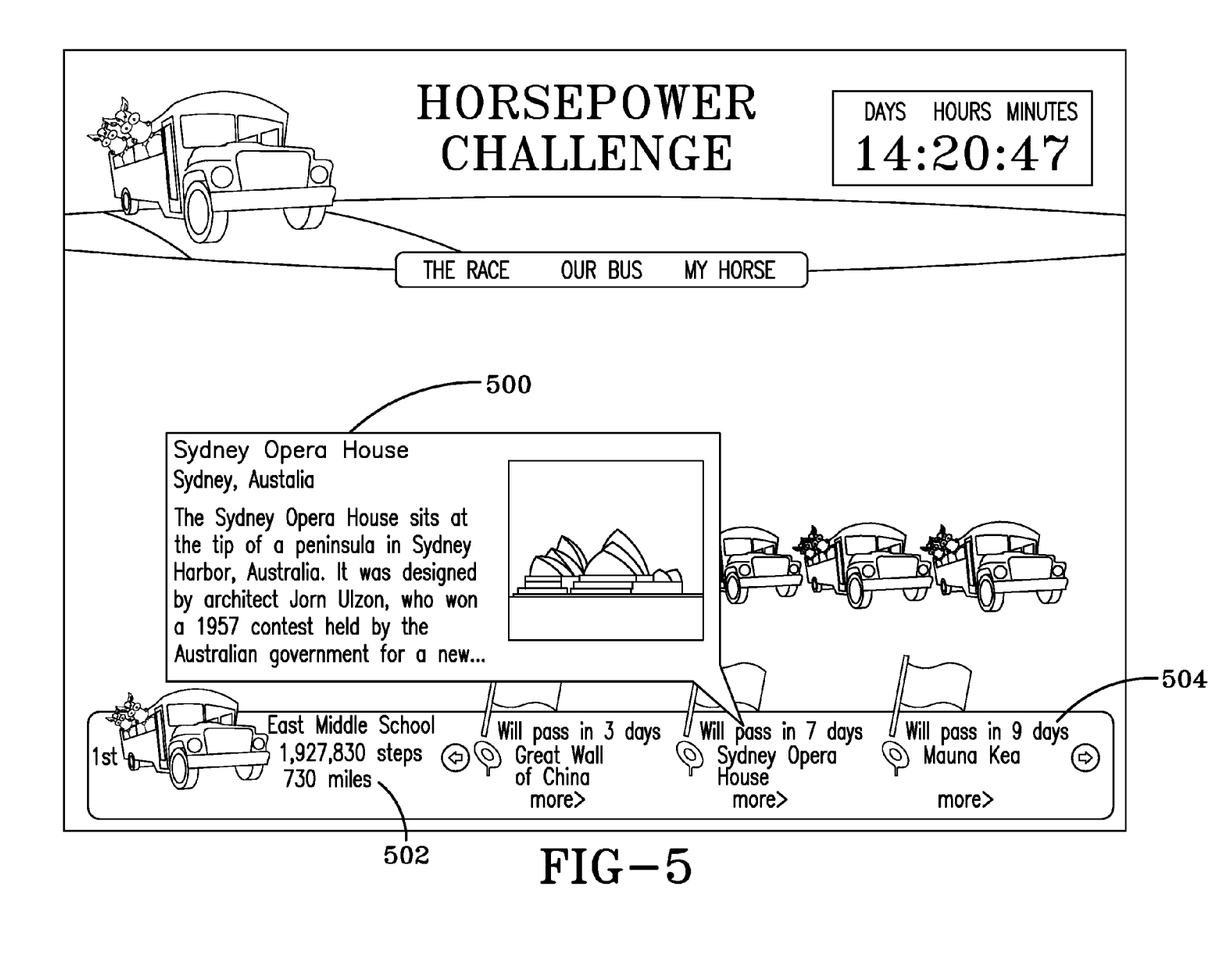
FIG. 5 is a sample checkpoint screen for an example embodiment.

Referring to FIG. 4, a sample bus screen for an example embodiment is shown. All of the screen characters for the students that belong to the school's team appear in the school bus. The bus moves past checkpoints in relation to the school's step activity. The individual step data for the students is combined to determine a total activity level (i.e., the number of miles that the students have collectively walked). The bus then moves to a new location in the world based on the applicable number of miles. The winner of the challenge is the team with the highest activity level based on the activity level of each individual team member. The winner also has the bus that travels the farthest during the challenge period. As each team's bus moves to a new location in the world, it passes one or more checkpoints. Students can view information about the checkpoints that their bus passes as shown in FIG. 5. Data about checkpoints is stored in the database and is associated with a particular step value or activity level. The school's step total is compared to the checkpoint step value to determine whether it has "passed" a particular checkpoint. Details about a particular checkpoint are shown in a popup window 500. In addition, a progress bar at the bottom of the screen shows the number of steps that the students have collectively walked and the applicable number of miles 502. Also shown is information for additional checkpoints as well as an estimate of the number of days until the bus will pass the landmark at the students' current step rate 504.

Other graphical objects or items such as cars, airplanes, or boats or any type of symbol or graphic may be used to represent each team. In addition, the object's movement from one location or setting to another may be tracked in many different ways including in relation to world landmarks, points in space, geographic locations, etc. Each time a user reviews team progress, the team's progress may be shown by displaying the team object in a representative location or setting where the location is determined according to the team's total activity level. Different locations or settings may be associated with a particular activity level, milestone, or checkpoint. The total activity level may then be used to determine the location or setting in which the team's graphical object should be displayed.

Figure 6:
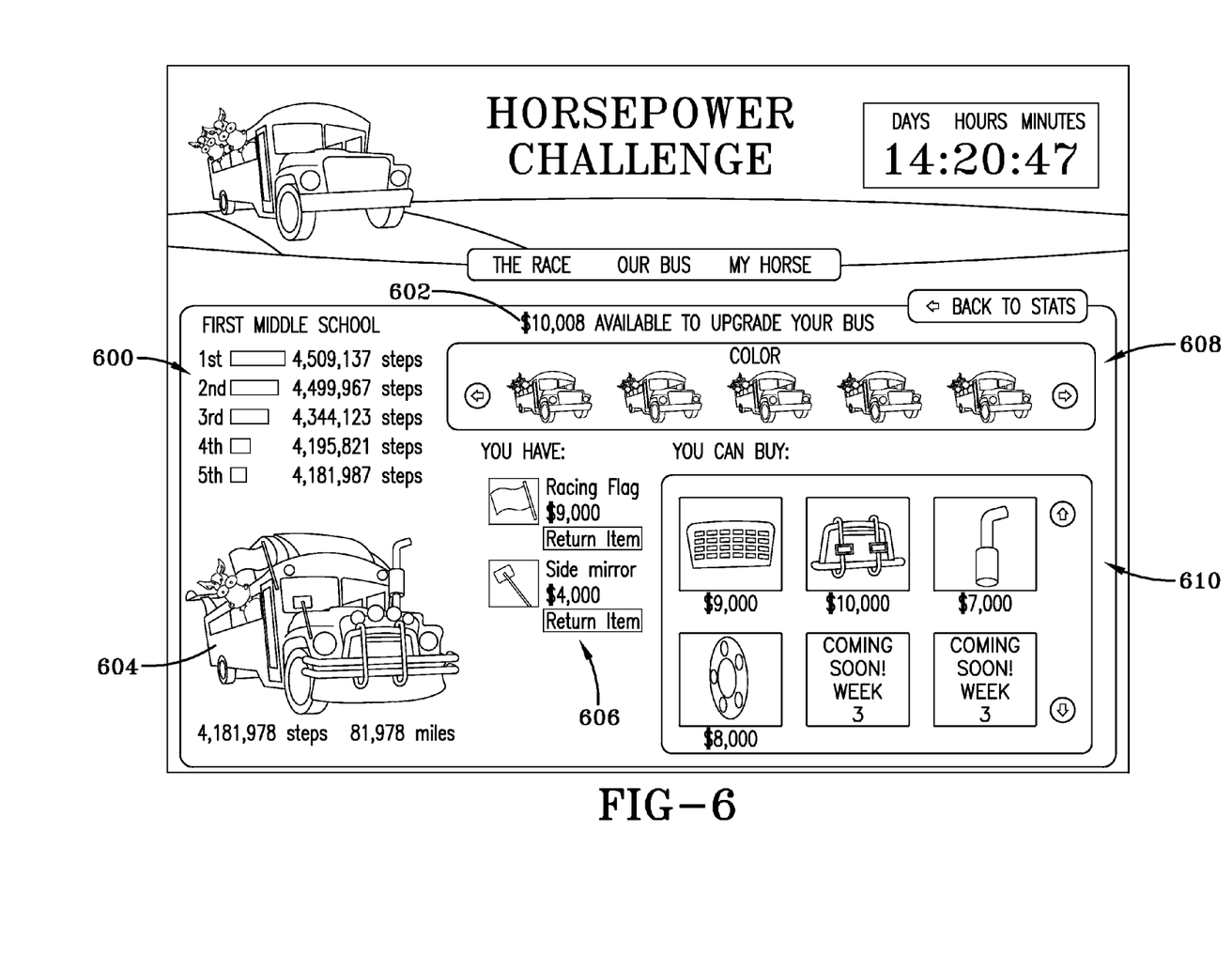
FIG. 6 is a sample upgrade bus screen for an example embodiment.

Referring to FIG. 6, a sample upgrade bus screen for an example embodiment is shown. The screen displays the current standings by team 600. The screen also indicates the amount available to the school for bus upgrades 602. The screen displays the school's bus 604 with its current upgrades and provides a scrolling list of the upgrades that the school has already purchased 606. Finally, the screen displays a scrolling list of upgrade options organized in groups or categories 608 as well as a detailed listing of upgrade options within a particular group or category 610. Upgrade options that the school selects are then applied to subsequent displays of the bus. The ability to upgrade the bus may be limited to a teacher or other school administrator through user permission features.

Figure 7:
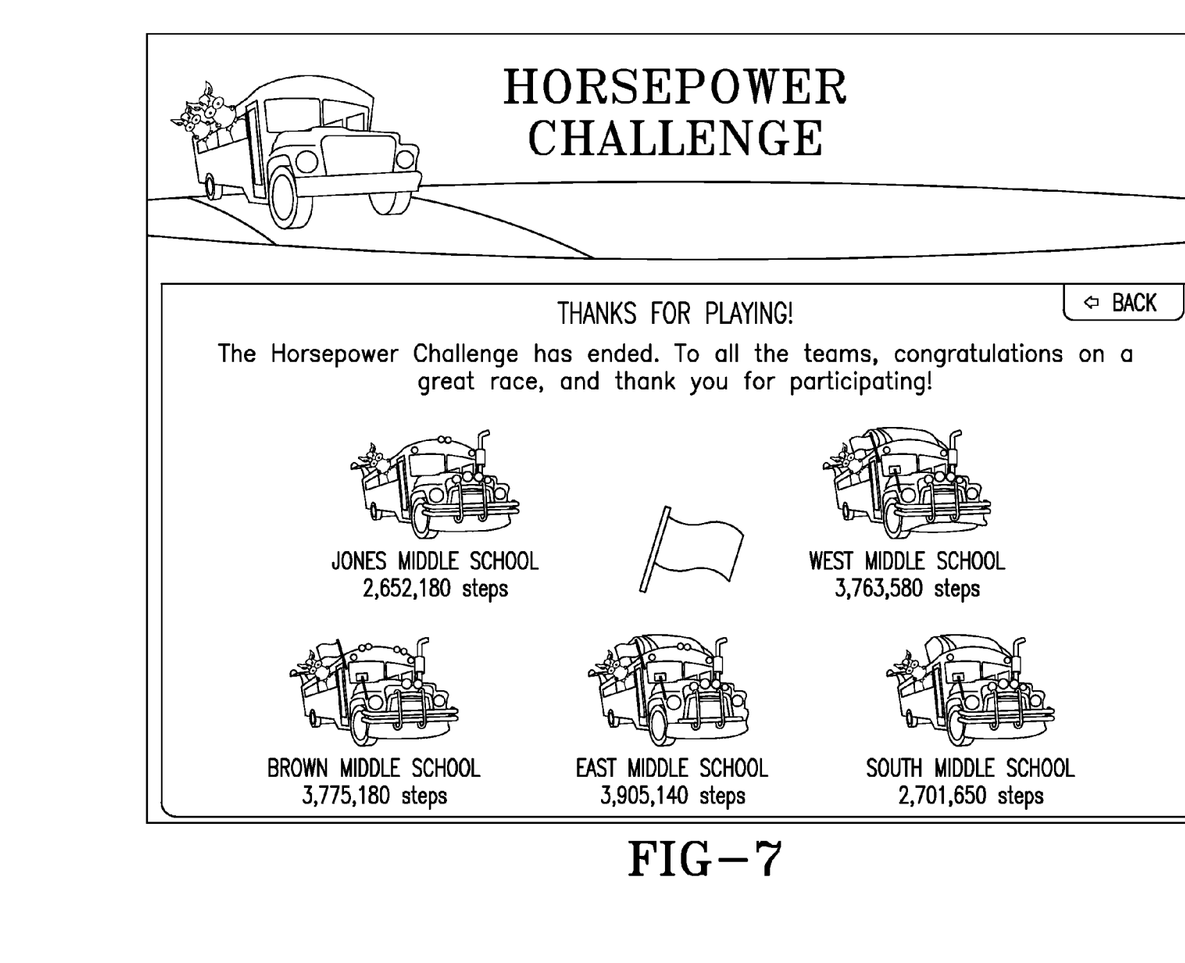
FIG. 7 is a sample results screen for an example embodiment.

Referring to FIG. 7, a challenge results screen for an example embodiment is shown. The results screen shows each team's bus and step total.

An administration component allows for the web based application administration of team data, user data, screen character data, bus data, and checkpoints. Referring to Tables 1-8, details for various administration screens of the administration component are shown.

Data for each team is entered and tracked. Team data includes a team identifier, team name, step total, timestamp for updates from the school remote access points where step activity for each student is collected, credits and debits for bus upgrades, and last payday. Edit and view options for each row of the screen allow an administrator to update data associated with a team.

TABLE 1

Teams Screen

| | Id | Name | Steps Total | Access Point Update | Credits | Debits | Last Payday |
|---|---|---|---|---|---|---|---|
| edit view | 2 | TEAM ABC | 4,028,190 | 2008-07-17 15:01:01 | 9,681 | 30,600 | 2008-06-09 00:01:02 |
| edit view | 3 | TEAM DEF | 4,450,130 | 2008-07-17 15:01:04 | 25,201 | 19,300 | 2008-05-29 14:01:22 |
| edit view | 4 | TEAM GHI | 5,082,480 | 2008-07-17 15:01:07 | 11,824 | 39,000 | 2008-07-17 15:01:07 |
| edit view | 5 | TEAM JKL | 3,313,080 | 2008-07-17 15:01:09 | 8,330 | 24,800 | 2008-05-23 07:01:19 |
| edit view | 6 | TEAM MNO | 3,199,770 | 2008-07-17 15:01:12 | 7,397 | 24,600 | 2008-05-24 11:01:25 |

Details for a selected team are shown in the following table. Details include the team identifier, an organization number, access point serial number, access point update timestamp, credits and debits for upgrades, step totals and step data by date, options data, and checkpoint crossing dates that indicate when the team crossed a particular checkpoint or landmark.

TABLE 2

Team Details Screen

| | |
|---|---|
| Id: | 2 |
| Organization: | 1 |
| Default Access Point Uploader Serial No.: | |
| Name: | TEAM ABC |
| Description: | |
| Last Access point Update: | 2008-07-17 15:01:01 |
| Next Access point Update start: | |
| Last Credits Update: | |
| Last Payday: | 2008-06-09 00:01:02 |
| Credits: | 9,681 |
| Debits: | 30,600 |
| Steps total: | 4,028,190 |
| Steps by date: | 2008-04-01: 181,372 |
| | 2008-04-02: 185,004 |
| | 2008-04-03: 163,056 |
| | 2008-04-04: 162,516 |
| | 2008-04-05: 114,660 |
| | 2008-04-06: 135,862 |
| | 2008-04-07: 104,488 |
| | 2008-04-08: 124,690 |
| | 2008-04-09: 76,096 |
| | 2008-04-10: 66,598 |
| | 2008-04-11: 54,494 |
| | 2008-04-12: 90,696 |
| | 2008-04-14: 109,576 |
| | 2008-04-15: 143,214 |
| | 2008-04-16: 138,324 |
| | 2008-04-17: 116,800 |
| | 2008-04-18: 200,860 |
| | 2008-04-19: 65,398 |
| | 2008-04-20: 76,068 |
| | 2008-04-21: 154,972 |
| | 2008-04-22: 161,584 |
| | 2008-04-23: 142,068 |
| | 2008-04-24: 125,342 |
| | 2008-04-25: 121,186 |
| | 2008-04-26: 69,396 |
| | 2008-04-27: 57,324 |
| | 2008-04-28: 95,660 |
| | 2008-04-29: 124,162 |
| | 2008-04-30: 118,404 |
| | . . . |
| | 2008-06-09: 514 |
| Options: | a:21:{i:46;b:1;i:74;b:1;i:83;b:1;i:77;b:1; i:73;b:1;i:56;b:0;i:102;b:1;i:81;b:1;i:106; b:1;i:113;b:1;i:116;b:1;i:61;b:1;i:103;b:1; i:70;b:1;i:47;b:0;i:48;b:0;i:49;b:0;i:45;b:0; i:44;b:0;i:43;b:0;i:50;b:0;} |
| Checkpoint crossing dates: | |

An administrator can also access a user screen to view data for individual users. Each user is associated with a team and has a user identifier as well as screen name. User data also includes a timestamp for the user's most recent sign-in and previous sign-in, a step total, and the serial number of the access point that receives the user's step data.

TABLE 3

User Screen: Part 1

| | Team | User ID | Screen Name | Most Recent Sign in | Previous Sign In | Steps Total | Access point Uploader Serial Number |
|---|---|---|---|---|---|---|---|
| edit view | 2 | 24 | USER1 | 2008-05-03 16:43:11 | 2008-05-01 14:07:36 | 229,334 | HHTK-00256-11425 |
| edit view | 2 | 25 | USER2 | 2008-05-05 11:21:33 | 2008-04-28 12:37:04 | 153,180 | HHRG-00256-12177 |
| edit view | 2 | 26 | USER3 | 2008-05-01 14:33:00 | 2008-04-28 12:24:38 | 277,610 | HHCW-00256-11512 |
| edit view | 2 | 27 | USER4 | 2008-05-05 20:47:46 | 2008-04-29 20:12:35 | 212,702 | HHXH-00256-11471 |
| edit view | 3 | 128 | USER5 | 2008-05-01 10:49:57 | 2008-05-01 09:12:44 | 243,029 | HHPQ-00256-11612 |

User data further includes a serial number for the user's pedometer, last access point update, next access point update, credit and debits for upgrades to his or her screen character, last credits update, last payday, and role. Edit and view options for each user entry allow an administrator to edit or view data for an individual user.

TABLE 4

User Screen: Part 2

|  | Team | User ID | Access point Actiped Serial Number | Last Access point Update | Next Access point Update Start | Credits | Debits | Last credits update | Last Payday | Role |
|---|---|---|---|---|---|---|---|---|---|---|
| edit view | 2 | 24 | FECJ-00256-29530 | 2008-07-17 15:01:01 | 2008-05-01 T00:00:00 | 593 | 1,700 |  | 2008-05-01 12:01:01 | User |
| edit view | 2 | 25 | FEWY-00256-29235 | 2008-07-17 15:01:01 | 2008-04-24 T00:00:00 | 31 | 1,500 |  | 2008-04-24 11:01:01 | User |
| edit view | 2 | 26 | FENM-00256-29146 | 2008-07-17 15:01:01 | 2008-05-01 T00:00:00 | 626 | 2,150 |  | 2008-05-01 11:01:01 | User |
| edit view | 2 | 27 | FEFW-00256-29056 | 2008-07-17 15:01:01 | 2008-05-01 T00:00:00 | 127 | 2,000 |  | 2008-05-01 11:01:01 | User |
| edit view | 3 | 128 |  |  |  | 0 | 0 |  |  | Team Admin |

User details include a user identifier, team identifier, sign-in data, access point user guide identifier, remote access point serial number, pedometer serial number, screen name, password, access point update timestamps, step data by date, credits update date, last payday, credits and debits, and options.

TABLE 5

User Details Screen

| | |
|---|---|
| Id: | 24 |
| Team: | 2 |
| Previous Sign In: | 2008-05-01 14:07:36 |
| This Sign In: | 2008-05-03 16:43:11 |
| Access Point User guide: | f24f1b10-9496-4410-a6fa-aee100fb821c |
| Access Point Uploader Serial No.: | HHTK-00256-11425 |
| Access point Actiped Serial No.: | FECJ-00256-29530 |
| Screen Name: | USER1 |
| Password: | ******** |
| Last Access point Update: | 2008-07-17 15:01:01 |
| Next Access point Update Start: | 2008-05-01 T00:00:00 |
| Steps Total: | 229334 |
| Steps by Date: | 2008-04-01: 8,566 |
| | 2008-04-02: 12,136 |
| | 2008-04-03: 22,546 |
| | 2008-04-04: 16,230 |
| | ... |
| | 2008-05-01: 10,018 |
| Last credits update: | |
| Last payday: | 2008-05-01 12:01:01 |
| Credits: | 593 |
| Debits: | 1700 |
| Options: | a:28:{i:20;b:0;i:21;b:0;i:22;b:0;i:31;b:0; i:33;b:0;i:15;b:0;i:16;b:0;i:19;b:0;i:24; b:0;i:34;b:1;i:35;b:0;i:37;b:0;i:36;b:0; i:32;b:0;i:30;b:0;i:14;b:0;i:18;b:0;i:23;b: 0;i:29;b:0;i:17;b:0;i:28;b:0;i:26;b:0;i:27; b:0;i:25;b:1;i:192 |

An administrator may also view comments as shown in the following table.

TABLE 6

User Comments Screen

| | |
|---|---|
| Id: | 15 |
| User: | 68 |

TABLE 6-continued

User Comments Screen

| | |
|---|---|
| Team Name: | TEAM ABC |
| Screen Name: | USER4 |
| Timestamp: | 2008-03-31 15:04:44 |
| Comment: | put more horse colors |
| Id: | 16 |
| User: | 40 |
| Team Name: | TEAM XYZ |
| Screen Name: | USER8 |
| Timestamp: | 2008-03-31 16:57:43 |
| Comment: | I can't seem to upload my steps with my ActiLink flashdrive at my house. What is the problem? - USER8 |

An administrator may also enter and view data for checkpoints related to landmarks throughout the world. Each checkpoint may have an associated step value for use in determining when a bus has passed a particular checkpoint.

TABLE 7

Checkpoint Screen

| Id | Asset | Name | Required Steps | Required Date |
|---|---|---|---|---|
| 1 | 1 | The White House | 100,000 | 2008-04-02 00:00:00 |
| 2 | 2 | Machu Picchu | 200,000 | 2008-04-04 00:00:00 |
| 3 | 3 | Serengeti Park | 300,000 | 2008-04-07 00:00:00 |
| 4 | 4 | Eiffel Tower | 500,000 | 2008-04-09 00:00:00 |
| 5 | 5 | The Great Sphinx | 1,400,000 | 2008-04-11 00:00:00 |
| 6 | 6 | Taj Mahal | 1,000,000 | 2008-04-15 00:00:00 |
| 7 | 7 | Great Wall of China | 1,200,000 | 2008-04-17 00:00:00 |
| 8 | 8 | Sydney Opera House | 0 | 2008-04-21 00:00:00 |
| 9 | 9 | Mauna Kea | 0 | 2008-04-23 00:00:00 |
| 10 | 10 | Easter Island | 0 | 2008-04-25 00:00:00 |
| 11 | 11 | Golden Gate Bridge | 250,000 | 2008-04-28 00:00:00 |

An administrator may edit and view data related to screen character or bus upgrades. Upgrades or assets are assigned a number, description, price, release date, and required number of steps. They are assigned to categories so they may be displayed according to category. "Can Buy" fields are used to indicate whether a team and/or user is permitted to purchase a particular asset. Edit and view options associated with assets allow an administrator to change or view details related to each asset.

TABLE 8

Upgrades Screen

|  | Id | Teams Can Buy | Users Can Buy | Asset Category | Asset | Name | Price | Release date | Release Steps |
|---|---|---|---|---|---|---|---|---|---|
| edit view | 1 |  | 1 | hat | 1 | 10 Gallon Hat | 250 | 2008-03-28 00:00:00 | 0 |
| edit view | 2 |  | 1 | hat | 2 | T Cap | 100 | 2008-04-03 00:00:00 | 0 |
| edit view | 3 |  | 1 | hat | 3 | Kentucky Hat | 150 | 2008-04-03 00:00:00 | 0 |
| edit view | 5 |  | 1 | mask | 1 | Sunglasses | 150 | 2008-04-01 00:00:00 | 0 |
| edit view | 6 |  | 1 | mask | 2 | Sunglasses | 150 | 2008-04-01 00:00:00 | 0 |
| edit view | 7 |  | 1 | mask | 3 | Sunglasses | 150 | 2008-04-01 00:00:00 | 0 |
| edit view | 14 |  | 1 | color | 1 | Color | 0 | 2008-03-13 22:14:02 |  |
| edit view | 15 |  | 1 | color | 2 | Color | 0 | 2008-03-13 22:14:02 |  |
| edit view | 16 |  | 1 | color | 3 | Color | 0 | 2008-03-13 22:14:02 |  |
| edit view | 30 |  | 1 | eyes | 1 | Eyes | 0 | 2008-03-13 22:14:02 |  |

The team-based fitness challenge system and method of the present invention allows students to participate in an entertaining and engaging activity that also encourages physical activity. Students are likely to enjoy the challenge because it uses computer technology with which they are familiar. Students can customize a screen character and monitor their own progress as well as their team's progress. The interface is easy and fun to use so students are likely to want to monitor their progress. In an example embodiment, the physical activity is one in which most children can engage—walking. Although the program may be sponsored by the school, the activity can be performed any time of day, in or out of school and alone or with others, including friends and family. As a result, students are more likely to perform the activity. The challenge also includes an educational component and allows children to learn about places around the world.

While certain embodiments of the present invention are described in detail above, the scope of the invention is not to be considered limited by such disclosure, and modifications are possible without departing from the spirit of the invention as evidenced by the claims. For example, other physical activities and related devices for measuring activity may be used and fall within the scope of the claimed invention. In addition, a variety of user and team screen characters may be used and fall within the scope of the claimed invention. One skilled in the art would recognize that such modifications are possible without departing from the scope of the claimed invention.

What is claimed is:

1. A fitness challenge system comprising:
   a plurality of activity measurement devices, wherein said devices automatically record activity level data for an activity performed by an individual using said activity measurement device and transfer said activity level data to a remote access point;
   a remote access point for receiving from said activity measurement devices activity level data for each individual using said activity measurement device;
   a server for receiving said activity level data from said remote access point;
   a database at said server for storing activity level data for each individual using said activity measurement device;
   a software application at said server for:
   (a) associating each one of a plurality of landmarks with an activity level;
   (b) establishing an account for each individual using said activity measurement device wherein said account holds identifying data for said activity measurement device and activity level data for said activity measurement device;
   (c) assigning each individual to one of a plurality of teams;
   (d) determining for each of said plurality of teams a total activity level based on activity level data for each individual assigned to each of said plurality of teams;
   (e) associating a graphical object with each of said plurality of teams;
   (f) selecting for each of said plurality of teams a landmark based on said total activity; and
   (g) creating a computer display screen with at least one graphical object for one of said plurality of teams wherein said object is shown in said landmark selected according to said total activity level for said team.

2. The system of claim 1 wherein said remote access point is located at a school.

3. The system of claim 2 wherein each individual using said activity measurement device is a student at said school.

4. The system of claim 1 wherein said graphical object associated with each of said plurality of teams is a school bus.

5. The system of claim 1 wherein said activity measurement devices are pedometers.

6. The system of claim 1 wherein establishing an account for each individual comprises associating a screen character with said account.

7. The system of claim 6 wherein said screen character is a horse.

8. A computerized method for encouraging physical activity comprising:
   (a) providing an activity measurement device to each of a plurality of individuals wherein said device automatically records activity level data for an activity performed by an individual using said activity measurement device and transfers said activity level data to a remote access point;
   (b) establishing at a server an account for each individual wherein said account holds identifying data for said activity measurement device assigned to said individual and activity level data for said activity measurement device;
   (c) storing in a database at said server for each of a plurality of landmarks an associated activity level;
   (d) receiving at least one remote access point from said activity measurement devices activity level data for each individual using said activity measurement device;
   (e) receiving at said server said activity level data from said remote access point;
   (f) storing at said server in said account for each individual activity level data from said activity measurement device;
   (g) assigning each individual to one of a plurality of teams;
   (h) determining for each of said plurality of teams a total activity level based on activity level data for each individual assigned to each of said plurality of teams;
   (i) selecting from said database for each of said teams a landmark based on said total activity level for said team; and
   (i) providing a computer display screen comprising
      (1) an identifier for each one of said plurality of teams; and
      (2) a landmark for each one of said plurality of teams selected from said database according to said total activity level for said team.

9. The method of claim 8 wherein said at least one remote access point is located at a school.

10. The method of claim 9 wherein each individual using said activity measurement device is a student at said school.

11. The method of claim 8 wherein providing a computer display screen comprising an identifier for each one of said plurality of teams comprises displaying a graphical object in association with each of said plurality of teams.

12. The method of claim 8 wherein said activity measurement devices are pedometers.

13. The method of claim 8 wherein establishing an account for each individual comprises associating a screen character with said account.

14. A fitness challenge method comprising:
   (a) providing an activity measurement device to each of a plurality of individuals wherein said device automatically records activity level data for an activity performed by an individual using said activity measurement device and transfers said activity level data to a remote access point;
   (b) establishing at a server an account for each individual wherein said account holds identifying data for said activity measurement device assigned to said individual and activity level data for said activity measurement device;
   (c) receiving at least one remote access point from said activity measurement devices activity level data for each individual using said activity measurement device;
   (d) receiving at said server said activity level data from said remote access point;
   (e) storing at said server in said account for each individual activity level data from said activity measurement device;
   (f) storing at said server a plurality of associations between an activity level and a location to be represented on a computer screen display;
   (g) assigning each individual to one of a plurality of teams;
   (h) determining for each of said plurality of teams a total activity level based on activity level data for each individual assigned to each of said plurality of teams;
   (i) associating a graphical object with each of said plurality of teams; and
   (j) providing a computer display screen with at least one graphical object for one of said plurality of teams wherein said object is shown in a representation of a location determined according to said total activity level for said team.

15. The method of claim 14 wherein said remote access point is located at a school.

16. The method of claim 15 wherein each individual using said activity measurement device is a student at said school.

17. The method of claim 14 wherein said graphical object associated with each of said plurality of teams is a school bus.

18. The method of claim 14 wherein said activity measurement devices are pedometers.

19. The method of claim 14 wherein establishing an account for each individual comprises associating a screen character with said account.

20. The method of claim 19 wherein said screen character is a horse.

* * * * *